US010407653B2

(12) United States Patent
Auner et al.

(10) Patent No.: US 10,407,653 B2
(45) Date of Patent: Sep. 10, 2019

(54) PHOTOBIOREACTOR

(71) Applicant: WAYNE STATE UNIVERSITY, Detroit, MI (US)

(72) Inventors: Gregory Auner, Livonia, MI (US); Michelle A. Brusatori, Sterling Heights, MI (US); Joseph M. Smolinski, Sterling Heights, MI (US); David J. Sant, Wixom, MI (US)

(73) Assignee: Wayne State University, Detroit, MI (US)

( * ) Notice: Subject to any disclaimer, the term of this patent is extended or adjusted under 35 U.S.C. 154(b) by 183 days.

(21) Appl. No.: 14/168,574

(22) Filed: Jan. 30, 2014

(65) Prior Publication Data

US 2014/0212954 A1    Jul. 31, 2014

Related U.S. Application Data

(60) Provisional application No. 61/758,998, filed on Jan. 31, 2013.

(51) Int. Cl.
 *C12M 1/00*    (2006.01)
(52) U.S. Cl.
 CPC .......... *C12M 21/02* (2013.01); *C12M 23/22* (2013.01); *C12M 29/04* (2013.01); *C12M 29/14* (2013.01);
(Continued)

(58) Field of Classification Search
 CPC ...... C12M 21/02; C12M 23/22; C12M 29/04; C12M 29/14; C12M 29/18; C12M 31/08; C12M 43/00; C12M 31/00; C12M 43/06
(Continued)

(56) References Cited

U.S. PATENT DOCUMENTS 5,031,990 A * 7/1991 Mori ...................... A01G 7/045
                                                          385/25
7,824,904 B1 * 11/2010 Dimanshteyn ......... C12M 21/02
                                                          435/292.1
(Continued)

FOREIGN PATENT DOCUMENTS

JP        05064578 A  *  3/1993  ............ C12M 21/02
KR    101043583 B1  *  6/2011  ............ C12M 21/02
(Continued)

OTHER PUBLICATIONS

Takizawa et al., English language machine translation of JP05064578A document, translated on Jun. 5, 2017.*
(Continued)

*Primary Examiner* — Liban M Hassan
(74) *Attorney, Agent, or Firm* — Brinks Gilson & Lione

(57) ABSTRACT

A photobioreactor system includes vessel for containing a biomass and a plurality of illuminators which may have solid state devices embedded therein or coupled thereto. The light energy is distributed in the vessel volume by the illuminators so as to reach substantially all of the biomass being circulated in the vessel. Biomass may exit the top of the vessel and be refreshed with nutrients and liquid before being reintroduced at the bottom of the vessel. Carbon dioxide is introduced at the bottom of the vessel. The biomass may be agitated either ultrasonically or by motion of the illuminators. A source of energy for the light sources may be solar panels with battery storage and the carbon dioxide may be a byproduct of thermal power generation.

14 Claims, 2 Drawing Sheets

(52) U.S. Cl.
CPC ............ *C12M 29/18* (2013.01); *C12M 31/08* (2013.01); *C12M 43/00* (2013.01)

(58) Field of Classification Search
USPC .......................................... 435/292.1, 257.1
See application file for complete search history.

(56) References Cited

U.S. PATENT DOCUMENTS

| | | | | |
|---|---|---|---|---|
| 2005/0260553 | A1* | 11/2005 | Berzin | C12M 43/06 |
| | | | | 435/292.1 |
| 2007/0264708 | A1* | 11/2007 | Bayless | C12M 43/06 |
| | | | | 435/292.1 |
| 2009/0130706 | A1* | 5/2009 | Berzin | C12M 21/02 |
| | | | | 435/292.1 |
| 2010/0279395 | A1* | 11/2010 | Haley, III | C12M 21/02 |
| | | | | 435/292.1 |
| 2012/0149091 | A1* | 6/2012 | Wilkerson | C12M 21/02 |
| | | | | 435/292.1 |
| 2013/0023044 | A1* | 1/2013 | Gleason | C12M 21/02 |
| | | | | 435/292.1 |

FOREIGN PATENT DOCUMENTS

| | | | | |
|---|---|---|---|---|
| WO | WO 201001401 A2 * | 2/2010 | ............ | C12M 21/02 |
| WO | WO-2010014010 A2 * | 2/2010 | ............ | C12M 21/02 |

OTHER PUBLICATIONS

Park et al., English language machine translation of KR 101043583B1 document, tranlsated on Jun. 1, 2017.*

* cited by examiner

PHOTOBIOREACTOR

The present application claims priority to U.S. provisional application Ser. No. 61/758,998, filed on Jan. 31, 2013, which is incorporated herein by reference.

TECHNICAL FIELD

This application relates to an apparatus and method of growing algae using a photobioreactor.

BACKGROUND

Raceway ponds are one of the simplest systems for mass cultivation of algae and have been used since the 1950's. In such a system, fresh culture medium is fed into an open pond where it cultured in natural environmental conditions. The pond is typically about 15-20 cm deep and is designed in a raceway configuration (a closed loop re-circulating channel). Pumps or a paddlewheel can circulate the algal cells and nutrients while baffles in the channel guide the flow around the bends in order to minimize space. The main disadvantage of an open system is the environment to which the pond and its contents are exposed. The pond is susceptible to evaporation, contamination by organic and inorganic sources, including unwanted biomaterial and proves to be problematic in maintaining optimum culture conditions. The open pond configuration also reduces the efficiency of microalgae use of carbon dioxide, thus limiting biomass production. Using sunlight as the energy source and being open to the environment, a limitation on the growing season and a diurnal and seasonal variability in the production rate may also be encountered depending on the geographic location.

Many different designs of enclosed photobioreactors (PBR) have been developed to overcome problems associated the open ponds, and some of the deficiencies have been mentioned above. Tubular reactors use ambient sunlight or can utilize an artificial light source as the energy source and are often considered for commercial large scale application. The reactors utilize arrays of long transparent tubes; however, the tube length is limited by pH variation, $O_2$ accumulation and $CO_2$ depletion. The tubes can be organized in a several configurations ranging from horizontal to helix.

Bubble column and airlift reactors are examples of vertical tubular reactors. Air is bubbled into the reactor at a bottom end to provide good mixing and sufficient $CO_2$ feedstock, while adequately removing $O_2$. This design offers an efficient gas transfer rate, but a major drawback of this reactor type is the angle of sunlight relative to the orientation of the tube; a large fraction of the incident light is reflected and not directed to the biomass being grown. The solar orientation with respect to the reactor changes diurnally and seasonally. Another drawback of this configuration is that the diameter of the tubes needs to be relatively large to provide high culture volume and efficient gas transfer. This decreases the area-to-volume ratio which decreases light utilization, thus decreasing the reactor efficiency compared with that of a flat panel reactor.

A reactor with a horizontal tube configuration allows more efficient light utilization than the vertical tubular reactor and unlike the vertical reactor typically has a gas transfer system. A drawback to this configuration is the orientation of the tubes. Although light harvesting increases, plot area required also increases, as well as the expense for the large number of tubes required to attain industrial scale volumes (5,000-10,000 L).

A helical tubular reactor is often configured with tubes coiled in an open circular framework. A centrifugal pump is used to circulate the culture thought the tubes. Although the technique has high light utilization, it is not as efficient as the flat panel. This is due to the orientation of the tubing relative to the sun; a fraction of the incident light is reflected and not directed to the biomass. Another drawback of this particular reactor is the use of a centrifugal pump; this can cause shear stress and hence cell damage.

Flat panel reactors are typically constructed with shallow depth panels to attain a high area-to-volume ratio. This design reduces the light path and increases light utilization efficiency. Algae cultures in these reactors are typically 2-4 cm thick with light being absorbed at the top of the culture within the first few millimeters, so only a fraction of the culture is being directly exposed to the incident energy. Systems have been constructed and tested using alveolar panels. The main disadvantage of this is oxygen buildup due to the small diameter of the reactor.

TABLE 1

Summary of the salient features of biomass production system design types.

| Reactor Design Type | Advantage | Disadvantage |
| --- | --- | --- |
| Raceway Ponds | Simple design<br>Fair to good mixing | Evaporation and contamination<br>Difficult species control<br>Low biomass production compared with photobioreactor [<br>Poor gas transfer<br>No temperature control |
| Vertical tubular reactor | Easy cultivation of microalgae<br>Most efficient gas transfer rate<br>Excellent temperature control | Difficult scale up. Dark zones are problematic in scale up.<br>Less efficient than flat panel reactor in light collection |
| Horizontal tubular reactor | Excellent light transfer<br>Excellent temperature control<br>Easy species control | Orientation of tubes requires more lands space than a vertical reactor.<br>Less efficient gas transfer rate than a vertical reactor |
| Helix tubular reactor | Small land area for large volumes<br>Uniform mixing<br>Excellent light utilization<br>Excellent temperature control | Less efficient than flat panel for light collection.<br>Pumping to drive the culture to the top of the tubing can cause cell damage. |
| Flat panel reactor | Supports the highest density of culture (high productivity).<br>Excellent light utilization<br>Excellent temperature control<br>High gas transfer rate<br>Uniform mixing | Oxygen build up<br>Difficult scale up |

Open systems such as raceway ponds, have the advantage of low capital cost, but photobioreactors offer better control of growth conditions, superior contamination control, and better containment of genetically modified organisms. In addition, photobioreactors may be used year-round, even in colder climates

SUMMARY

A photobioreactor system is disclosed having a container with a large vertical dimension than either of the principle horizontal dimensions. The top and the bottom of the container, which may have a cylindrical form, may be closed on the bottom by a watertight closure, and have a top closure. Within the container an illuminator assembly is disposed, having a plurality of horizontal sheets each spaced a distance apart from an adjacent horizontal sheet. The sheets may have a plurality of apertures formed therein so as to permit fluid flow between opposing sides of the sheets. Light sources may be a part of the illuminator assembly or light from light sources may be coupled to the illuminator assembly so as to be emitted into the volume between the sheets.

An actuator, which may be a piezoelectric device or a mechanical transport mechanism may be coupled to the illuminator so as to mover the illuminator reciprocally in a vertical direction. An inlet at a bottom portion of the photobioreactor may be adapted to receive a pressurized gas.

In an aspect, the horizontal sheets of the illuminator may formed of substantially clear optical material and include light sources which may be one or more types of a laser or light emitting diode, selected such that the central wavelength of the emitted light is efficiently coupled to the type of biomass feedstock being used.

The photosynthesis process in an algae feedstock may be more efficient when the light source is pulsed such that a peak light intensity substantially greater than an average light intensity is achieved.

Circulation of the biomass is intended to be from bottom to top of the container, and an outlet at the top of the container through a pipe 115 is provided so that the biomass, having passed through the container may be drawn off and harvested, or refreshed with nutrients, water or seed feedstock. The refreshed biomass is introduced into the bottom of the container by gravity feed or a pump 40 and encouraged to flow in a vertical direction in the container.

Carbon dioxide gas, as photosynthesis feedstock may be provided under pressure and bubbled through the liquid biomass so as to distribute the gas as well as encourage the vertical circulation of the liquid. The source of the carbon dioxide may be conventional air liquefaction or it may derive, for example from a co-located thermal (coal or gas) electrical power generation facility. Electrical power to operate the photobioreactor may be provided by an electrical power generation facility, solar cells and a storage battery, or other economically viable source.

A method of growing biomass in a photobioreactor is disclosed including: providing a photobioreactor vessel having a elongate vertical dimension and closable at a top end and a bottom end, with an electrically powered light source having a light source emission with a central wavelength selected to couple light energy to the biomass through an illuminator assembly having a plurality of horizontal surfaces spaced apart in a vertical direction.

In an aspect, the method may include introducing the biomass feedstock in a liquid at the bottom portion of the photobioreactor along with carbon dioxide, such that the liquid medium circulates from the bottom to the top of the device.

Further, the method may comprise gently agitating the biomaterial using an agitator, which may be the illuminator. After circulating to the top of the container of the photobioreactor, the biomaterial may be drawn off and processed such as harvesting the biomaterial, refreshing the biomaterial and the lime may be performed prior to reintroducing the liquid into the container.

The method may also include providing carbon dioxide gas that is derived from a co-located thermal power plant, and some or all of the electrical energy from solar cells and battery storage.

DESCRIPTION

Exemplary embodiments may be better understood with reference to the drawings, but these examples are not intended to be of a limiting nature. Like numbered elements in the same or different drawings perform equivalent functions. When a specific feature, structure, or characteristic is described in connection with an example, it will be understood that one skilled in the art may use such a feature, structure, or characteristic in connection with other examples, whether or not explicitly stated herein.

A closed-system photobioreactor (PBR) needs to consider at least the following technological and biological criteria: (1) provide a closed environment with effective introduction of $CO_2$ and biomass feedstock; (2) have an efficient source of light energy, optimized for algae growth, including intensity control and wavelength selection; (3) an agitation system for stimulating algae mixing and growth as well as antifouling capabilities; and a (5) a prime power system minimizing environmental impact. The resultant system may have the prospect of being operated in an economically feasible manner, taking all costs and benefits into account.

Figure 1:
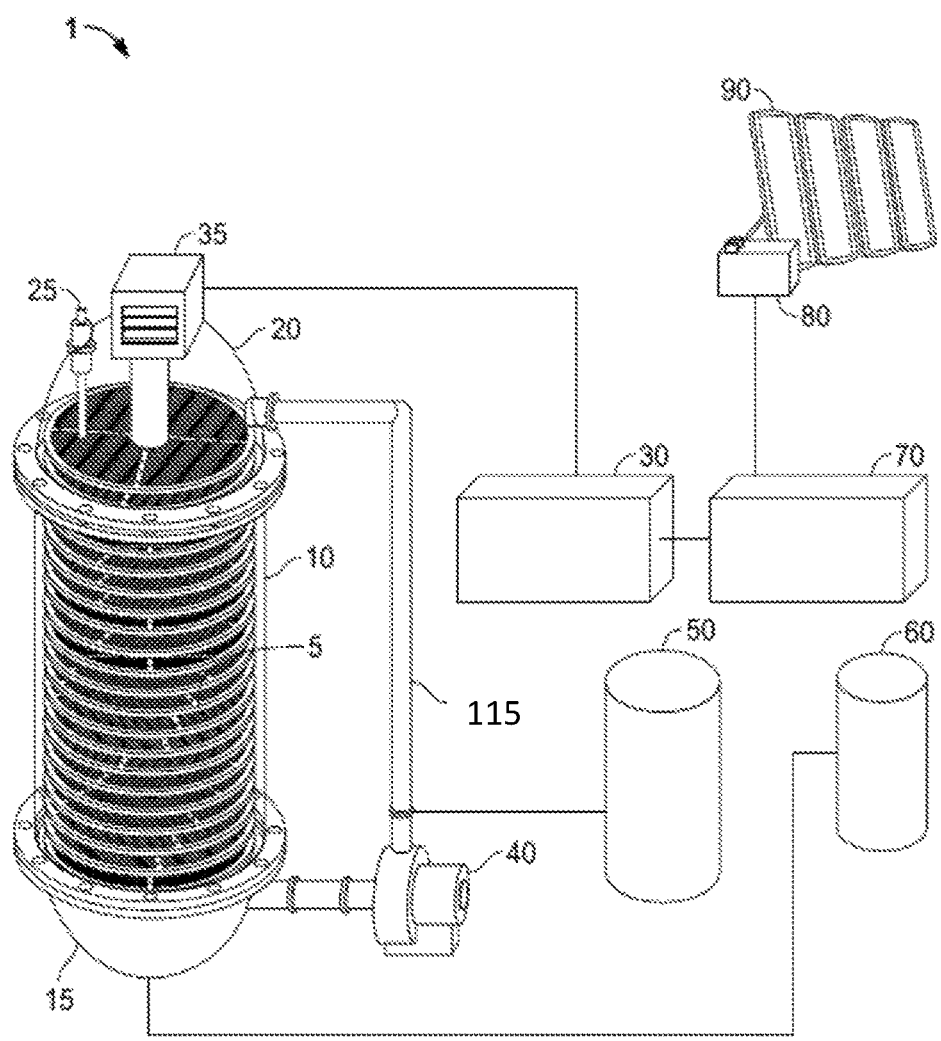
FIG. 1 is a schematic representation of a photobioreactor system showing the reaction chamber, potential sources of energy and feed stock and the orientation of the illuminators in the chamber.

FIG. 1 is a representative conceptual drawing of a photobioreactor system, showing an example, which may be one of a plurality of photobioreactors using a solar panel system as the prime source of power. The source of $CO_2$ may be, for example, conventional ambient gas liquefaction, or be the byproduct of exhaust gas sequestration in a collocated power plant, or the exhaust gas. The $CO_2$ gas may be produced either on site or at another facility. Where exhaust gas sequestration on site is used, for example, this may be a symbiotic relationship being a useful alternative to other means of reducing $CO_2$ emissions by a fossil fuel power plant.

Figure 2:
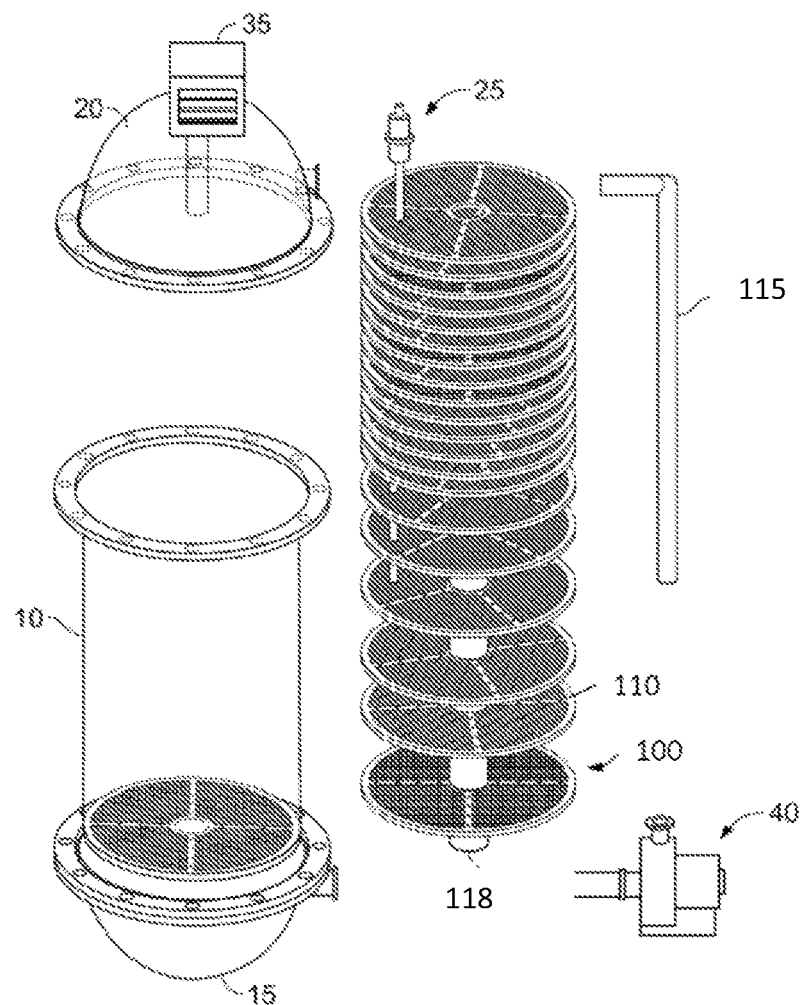
FIG. 2 is an exploded view of the reaction chamber that shows the arrangement of illuminators and a possible configuration where the reaction chamber may be disassembled for cleaning.

The photobioreactor system 1 of FIG. 1 may comprise the photobioreactor container 5, details of which are shown in FIG. 2, where the photobioreactor (PBR) 5 is a structure having an enclosure 10, which may be a tube or other shaped vessel, such as a rectangular cross section, and having a greater dimension in a vertical direction. A bottom portion of the enclosure may be a watertight closure 15 secured to the body of the enclosure 10. The closure may be disassembled for servicing. A top cap 20 may prevent spillage and serve to contain or regulate gasses evolved from the top of the biomaterial present in the photobioreactor container 5 during operation. An inlet 45 at a bottom portion of the photobioreactor may be adapted to receive a pressurized gas and an outlet at the top 46 is provided so that the biomass, having passed through the container may be drawn off and harvested, or refreshed with nutrients, water or seed feedstock.

A control and monitoring electronics subsystem 30 may provide for regulating the amount of the materials such as feedstock, nutrients, water and carbon dioxide, and using light sensor 25 (optional) to determine the amount of energy supplied to the photobioreactor based on the ambient light conditions. The control and monitoring system 30 may also regulate the power for the light sources and control the agitation or circulation mechanisms. The operation of the control and monitoring electronics subsystem 30 is described below.

The energy source for operation of the system may be either entirely derived from a photovoltaic system 90 or be a combination of ambient light and photovoltaic energy sources. Other conventional sources of power may also be used.

Where the photovoltaic system (solar panels) are used, the energy may be, in part, temporarily stored in an energy storage system 70, which may include storage batteries, to accommodate the diurnal variation in energy production. Typically the output of the solar cells is conditioned by electronics 80 for storage in the energy storage system 70, although some of the solar panel energy may be used directly by the photobioreactor 5. The energy storage system 70 may be comprised of storage batteries such as valve-regulated lead acid batteries (VRLA), nickel-cadmium (Ni-Cad) batteries, lithium-ion batteries, or the like, depending on the scale size of the installation. Other energy storage systems that are known or may be developed for diurnal storage of solar-produced energy may also be used.

The energy storage system 70 may be integral to the photobioreactor system or be shared with other systems, including a thermal electric power plant itself as a more integrated overall power supply management process.

Each of the components of the power system, such as the solar cells (for example) 90 and the battery system 70 may have a different conversion efficiency and the overall solar-to-electrical conversion efficiency is such that a lower energy recovery is achieved with respect to the efficiency of each component individually. However, the conversion of the solar spectrum incident on the solar cells to an electrical form may facilitate the more efficient use of a generated artificial illumination spectrum for growing the biomass using photosynthesis.

Photosynthesis is facilitated by a choice of the illumination wavelength spectrum to match the photoactivity of a selected algae type, and the management of the illumination intensity, including both the short and long term temporal characteristics of the illumination intensity. Use of an energy storage system 70 allows the energy to be delivered as needed and at an optimal rate determined for the particular process or the stage of the process. This may permit the photobioreactor to operate with an efficient light-dark cycle and illumination intensity, not subject to diurnal variations. A power plant or a commercial electrical grid may sometimes also be used as the source of power at times when the economics are favorable.

When the biomass density is increased by the photosynthesis process, the mean-free-path of the illumination energy within the growing medium is decreased, as the illumination energy is absorbed, limiting efficient photosynthesis to the biomass to near the light source. Thus the growth properties of the biomass within the photobioreactor may have spatial and temporal variations that are a problem to effectively manage. In the case of sunlight, it is somewhat inconvenient to illuminate a tube, for example for all sides, and the diameter of the tube would be limited, and the temporal input of energy is affected both by diurnal, seasonal and weather-related factors. However, when artificial illumination is available, the overall energy input may be monitored and controlled.

A laser or light-emitting diode (LED) may be selected so as to emit energy at wavelengths associated with high utilization of the energy for photosynthesis by the selected growth medium. The light energy may be routed to desired locations with respect to the biomass, including within the PBR 5, using free space optics, bulk optics, or fiber optics, so as to mitigate the effects of light scattering and absorption and make best use of the PBR volume. Alternatively, a plurality of light energy sources may be distributed throughout the PBR volume so as to provide an effective illumination density profile. The light sources, when located within the PBR, may be energized with energy provided by the energy storage system or the solar panels, or the like. Any light energy that is not used in the photosynthesis process, and does not escape the system through the side walls of the container, will be converted to thermal energy, as well as a portion of the electrical energy that was used to excite the light source but was not converted into light output. The light that was not absorbed may be permitted to escape from the PBR through transparent sides of the container 10, or may be reflected back into the PBR by reflective coatings deposited on the sides of the container 10. Alternatively, for example, an opaque column surface with a reflecting coating may be used. The column may be made of a plastic, or a metal, and may have internal coatings that are intended to minimize attachment of the biomass to the walls thereof. During the growth phase, the light intensity and other characteristics may be managed so as to most effectively use the prime energy sources. If a combination of ambient and artificial light is to be used, this may be regulated by a light sensor 25, taking account of the differing spectral content of the natural and artificial light sources.

With an electrically driven source of light is used, the intensity and the temporal characteristics of the light, as well as its wavelength may be well controlled, on a scale time varying from microseconds to days. As a most effective illumination profile may differ at various stages of the growth process, particularly if a batch process is used, control of the illumination results in an improved use of the prime power source. For example, the intensity of the artificial light may be increased as the density of the biomass increases so as to maintain a more constant flux per algae cell.

The photosynthesis process is known to saturate above a particular average illumination flux; however, the scale-time of the photosynthesis reaction is believed to be on the time scale of tens of microseconds, and thus a pulsed light source may be more effective than a continuous source, and this is conveniently achievable with solid state light sources such as LEDs or lasers. Moreover, by using a plurality of such sources and scheduling the pulsing periods with respect to each other, the average power demand may be smoothed, which would contribute to smaller conductor sizes and lower peak power demands on the power supply, while delivering an optimal energy flux to the biomass. Recalling that photons that are not absorbed and used in the photosynthesis process would be converted into thermal energy, this is a consideration both in the growth rate of the biomass and the overall efficiency of the process.

FIG. 2 is an exploded view of the bioreactor element 5 of the photobioreactor system 1: a container which may be an outer tube 10, and bottom 15 and top closures 20. The closures are shown as dome shaped, but may be cylindrical or other shape. A plurality of polycarbonate (or other optically transparent material) disks 100 may be disposed along the length of the PBR vessel and spaced at a distance of about 2.5 cm, although other vertical spacing may also be used. The disks may be horizontally disposed sheets 110 and may serve to distribute light energy from a light source, which may be a plurality of light sources, to the vicinity of each of the disks, so as to reduce the absorption path length between the light energy source and the absorbing biomass and more uniformly distribute the energy over the volume. In addition to facets on the surface of the polycarbonate disks to effectively radiate the light energy, the disks may be perforated with apertures over perhaps 80 percent of the disk area so as to permit the flow of the biomass and surrounding fluid along the vertical length of the PBR. A large number of apertures in each disk may reduce the flow resistance and the turbulence of the flow, which may minimize physical damage to the cells of the biomass. The horizontal sheets of the illuminator may formed of substantially clear optical material and may include a light source disposed such that the light emitted by the light source is radiated into a volume between adjacent horizontal sheets of the plurality of horizontal sheets. The source of emitted light energy may be a light emitting diode or a laser having a central wavelength selected to cause energy transfer to a selected biomass feedstock.

Alternatively, where a plurality of light sources are distributed within the interior of the PBR, the disks 100 may be metallic and may be coated with material so as to inhibit attachment of the biomass. The light sources may be attached to the disks 100.

At the top of the bioreactor outer tube 10, the biomass and fluid may drained off and recirculated after excess O2 is drawn off and nutrients and water volume renewed from a reservoir 50. Oxygen is a product of photosynthesis but is an inhibitor of algal growth. Thus, the produced oxygen needs to be removed to prevent produced oxygen from reaching levels that interfere with the photosynthesis process. A sparging process may be used. This may be by bubbling a compressed gas such as the carbon dioxide from a reservoir 60 into the biomass at the bottom of the bioreactor outer tube 10, or by gentle agitation using the disks 110, or other mechanical means. The agitation may be provided by piezoelectric forcers or other mechanical actuators that are part of an interface assembly 35 at the top of the PBR. The agitators may be mounted internally to the container 10, and may be the horizontally disposed circular sheets 110.

The refreshed biomass may be injected at the bottom portion of the PBR along with $CO_2$, which may be bubbled into the PBR. In a batch processing approach, once the biomass density has reached a harvestable amount, the biomass may be drained from the PBR and further processed. Alternatively the PBR may be operated as a continuous process and after a suitable biomass density is reached, a portion of the biomass may be continually harvested as the material is being recirculated so as to keep a steady-state condition. Since the initial phase of growth is likely to have exponential characteristics, an initial biomass starter culture having some minimum algae load may be used in order to improve the overall efficiency of the process. This starter culture may be a portion of a previous production batch.

The laser diodes or other light source such as LEDs may be mounted, for example, in housing 35, external to the bioreactor and the polycarbonate material, along with a central light pipe or support column 118 to which the plurality of disks 100 are attached may be used to distribute the light. Alternatively, light sources may be associated with individual disks or groups of disks, and locally mounted thereto, so that only electrical power needs to be supplied. Light sources having different central wavelengths may be used and controlled so as to effectively supplement any ambient lighting used.

Algae fouling of the surfaces of the polycarbonate disks 100 may occur and may be mitigated by, for example, coating the surfaces with a fluorocarbon coating and periodically agitating the disks using a sonic source. The frequency of the agitation and the intensity of the agitation may be chosen so as to minimize the rate of fouling while also avoiding significant physical damage to the algae. Other means of cleaning the surface of the disks, such as a wiper system where a set of wiper blades is occasionally rotated with respect to the disks 100 to clean the top and bottom surfaces. Alternatively the disks may be rotated with respect to fixed wiper or squeegee blades. Additionally, the disk array assembly may be slowly oscillated in a vertical direction using the column 110 so as to increase the relative speed of motion of the biomass over the horizontal surfaces, which may contribute to both more efficient mixing and less biofouling.

Process control using the control and monitoring electronics 30 for the PBR may include monitoring a number of environmental parameters including temperature, extinction distance, or the like, which may be used to regulate the supply of nutrients, the light intensity and time profile, the recirculation rate, the supply of $CO_2$ and the like. The waste heat from a thermal electric power generation may be used as energy for temperature control of the photobioreactor Photosensors may measure the absorption of a light beam propagating between either two disks or the central column 118 and the side wall, so as to estimate the biomass density. Such sensors may be disposed at a number of vertical distances along the height of the PBR. This sensor may also be used to estimate the amount of biofouling so as to regulate cleaning cycles. For such cleaning cycles the top 20 or the bottom 15 covers may be removed and the column 118 used to extract the disk array 100 from the container 10.

$CO_2$ levels and oxygen levels and temperature may also be monitored and the $CO_2$ bubbler adjusted to maintain an appropriate gas feed level as well as to gently agitate the biomass and aid in the circulation. In addition, concentrations of nitrogen, phosphorus, sulfur and trace minerals, temperature, pH may be monitored so as to control the nutrient dosage. An active pumping scheme may be used; however passive gravity-type circulation systems are less damaging to the cells of the biomass.

The algae culture types may be selected using measures of photo-efficiency and the match of the absorption efficiency to the wavelength of the optical source as well as the properties of the harvested biomass. Sometimes the choice may be governed by the relative cost of optical source having particular wavelength characteristics. For example, the algae in Table 2 are sources of biomass that have good absorptive spectrum profiles and a sufficient yield to be considered in designing a system.

TABLE 2

Examples of Biomass Types

| Microalgae | Oil content (% dry wt) |
|---|---|
| *Botryococcus braunii* | 25-75 |
| *Chlorella* sp. | 28-32 |
| *Crypthecodinium cohnii* | 20 |

TABLE 2-continued

Examples of Biomass Types

| Microalgae | Oil content (% dry wt) |
|---|---|
| Cylindrotheca sp. | 16-37 |
| Dunaliella primolecta | 23 |
| Isochrysis sp. | 25-33 |
| Monallanthus salina | >20 |
| Nannochloris sp. | 20-35 |
| Nannochloropsis sp. | 31-68 |
| Neochloris oleoabundans | 35-54 |
| Nitzschia sp. | 45-47 |
| Phaeodactylum tricornutum | 20-30 |
| Schizochytrium sp. | 50-77 |
| Tetraselmis sueica | 15-23 |

Although only a few exemplary embodiments of this invention have been described in detail above, those skilled in the art will readily appreciate that many modifications are possible in the exemplary embodiments without materially departing from the novel teachings and advantages of the invention. Accordingly, all such modifications are intended to be included within the scope of this invention as defined in the following claims.

What is claimed is:

1. A system, comprising:
a photobioreactor having:
a container having a vertical dimension greater than any linear horizontal direction and having a top end and a bottom end thereof;
a top closure and a watertight bottom closure disposed to cover the top end and the bottom end of the container, respectively;
an illuminator assembly comprising one or more light sources and at least 3 horizontal sheets, each of said at least 3 horizontal sheets is coupled to said one or more light sources and configured to radiate light energy form said one or more light sources into the photobioreactor, wherein said at least 3 horizontal sheets are spaced apart along a vertical support by a vertical distance;
an actuator coupled to the vertical support configured to oscillate the illuminator assembly in a direction orthogonal to a surface of each sheet of the at least 3 horizontal sheets as a group of sheets; and
a first inlet at a bottom portion of the photobioreactor configured to receive a pressurized gas,
wherein a second inlet at the bottom portion of the container is configured to permit a liquid to flow into the container and an outlet at the top end of the container is configured to permit a liquid to flow out of the container;
each sheet of the at least 3 horizontal sheets has a plurality of apertures formed through about 80 percent of a surface area of the sheet, each of said plurality of apertures is configured to permit fluid flow between opposing sides of each of the at least 3 horizontal sheets, and
wherein said light energy is radiated into a volume between adjacent horizontal sheets of the at least 3 horizontal sheets through said surface area of each of said at least 3 horizontal sheets.

2. The system of claim 1, wherein said one or more light sources include a light emitting diode or a laser having a central wavelength selected to cause energy transfer to a selected biomass feedstock.

3. The system of claim 2, wherein said one or more light sources emit pulsed light.

4. The system of claim 3 where the selected biomass feedstock is an algae.

5. The system of claim 1, wherein the system is configured to add a nutrient to a biomass prior to the biomass being reintroduced at the bottom end of the photobioreactor.

6. The system of claim 1, wherein the pressurized gas is carbon dioxide.

7. The system of claim 1, wherein the pressurized gas comprises a carbon dioxide gas that is a byproduct of a thermal electrical power generation system.

8. The system of claim 7, wherein an electrical power source for the illuminator assembly comprises a solar cell and a storage battery.

9. The system of claim 1, wherein the system is configured to use waste heat from a thermal electric power generation as energy for temperature control of the photobioreactor.

10. The system of claim 1, wherein said vertical spacing between adjacent sheets of the at least 3 horizontal sheets is about 2.5 cm.

11. The system of claim 2, wherein each sheet of the at least 3 horizontal sheets are fabricated from a polycarbonate or other optically transparent material at the central wavelength of the one or more light sources.

12. The system of claim 3, wherein a duration of the pulsed light is tens of microseconds.

13. The system of claim 12, wherein the one or more light sources comprises a plurality of pulsed light sources and the pulsed sources are scheduled to reduce a peak-to-average power consumption of the plurality of pulsed light sources.

14. The system of claim 1, wherein the container is filled with water.

* * * * *